(12) United States Patent
Fallin

(10) Patent No.: US 6,666,868 B2
(45) Date of Patent: Dec. 23, 2003

(54) TWO-PART ORTHOPEDIC FASTENER

(75) Inventor: T. Wade Fallin, Hyde Park, UT (US)

(73) Assignee: MedicineLodge, Inc., Logan, UT (US)

( * ) Notice: Subject to any disclaimer, the term of this patent is extended or adjusted under 35 U.S.C. 154(b) by 0 days.

(21) Appl. No.: 09/798,300

(22) Filed: Mar. 2, 2001

(65) Prior Publication Data
US 2002/0123751 A1 Sep. 5, 2002

(51) Int. Cl.[7] ............................................. A61B 17/84
(52) U.S. Cl. ....................................................... 606/73
(58) Field of Search ............................. 606/72, 73, 76, 606/77; 411/900, 904; 433/173

(56) References Cited

U.S. PATENT DOCUMENTS

| | | | |
|---|---|---|---|
| 3,693,495 A | * 9/1972 | Wagner ........................ 411/377 |
| 4,338,926 A | 7/1982 | Kummer et al. |
| 4,478,904 A | * 10/1984 | Ducheyne et al. |
| 5,013,315 A | 5/1991 | Barrows |
| 5,098,434 A | * 3/1992 | Serbousek ................... 606/73 |
| 5,374,268 A | 12/1994 | Sander |
| 5,632,745 A | * 5/1997 | Schwartz .................... 606/75 |
| 5,713,903 A | 2/1998 | Sander et al. |
| 5,720,753 A | 2/1998 | Sander et al. |
| 5,935,127 A | 8/1999 | Border |
| 5,964,783 A | 10/1999 | Grafton et al. |
| 5,968,047 A | * 10/1999 | Reed ........................... 606/76 |
| 6,007,287 A | * 12/1999 | Toosky et al. .............. 411/504 |
| 6,022,352 A | 2/2000 | Vanderwalle |
| 6,027,523 A | 2/2000 | Schmieding |
| 6,162,225 A | * 12/2000 | Gertzman et al. ............ 606/73 |
| 6,319,252 B1 | 11/2001 | McDevitt et al. |
| 6,436,110 B2 | 8/2002 | Bowman et al. |

FOREIGN PATENT DOCUMENTS

JP          10085232          4/1998

* cited by examiner

Primary Examiner—Kevin Shaver
Assistant Examiner—Michael B. Priddy
(74) Attorney, Agent, or Firm—Pandiscio & Pandiscio P.C.

(57) ABSTRACT

The present invention comprises the provision and use of a novel orthopedic fastener. The novel orthopedic fastener comprises a body portion adapted to extend substantially below the surface of a bone, and a head portion adapted to extend substantially above the surface of the bone, wherein the body portion is formed of a first material and the head portion is formed of a second material. In one preferred form of the invention, the first material comprises a bioabsorbable material which is bioactive so as to encourage tissue in-growth, and the second material comprises a bioabsorbable material which is not bioactive so as to not encourage tissue in-growth.

8 Claims, 18 Drawing Sheets

TWO-PART ORTHOPEDIC FASTENER

BACKGROUND OF THE INVENTION

1. Field of the Invention

This invention relates to medical devices in general, and more particularly to orthopedic fasteners for securing bone or soft tissue to bone.

2. Description of Related Art

Many clinically-successful treatments exist for repairing fractured bones and for re-attaching soft tissue to bone. These treatments typically involve the use of a fixation device to secure bone to bone or soft tissue to bone. By way of example, bone fractures are commonly repaired using plates and screws, cerclage wires, intramedullary rods, and external fixation devices. By way of further example, soft tissue re-attachments are commonly effected using suture anchors to suture the soft tissue to bone, headed fasteners that pierce the soft tissue and anchor in bone, and fasteners that lock the soft tissue within a bone hole.

In general, when repairing fractured bones and re-attaching soft tissue to bone, the fixation device only needs to be used in the near term. Once the bone fracture has healed or the soft tissue has biologically re-attached itself to bone, the fixation device is no longer required. In fact, the continued presence of the fixation device within the body is often detrimental to the patient, as it may interfere with the natural physiology of the patient. More particularly, in many cases, the fixation device shields the musculoskeletal structure from physiological forces. This "stress shielding" typically leads to weaker tissue structures; in the case of bone tissue, for example, "stress shielding" commonly leads to reduced bone mineral density, and can lead to morphological changes in cortical bone thickness and cancellous bone trabeculi.

In view of such "stress shielding" concerns and other physiological concerns, and in view of the fact that many fixation devices may be palpable under the skin, and in view of the fact that many fixation devices are made from metals which can interfere with certain types of diagnostic imaging (e.g., MRI imaging), the fixation device is often removed after healing is complete. However, this necessitates a second surgery, which is accompanied by patient discomfort, risk of complications, etc.

In an effort to address the foregoing concerns, fixation devices have been fabricated from biodegradable materials. Biodegradable orthopedic fixation devices have most commonly been produced from aliphatic polyesters of poly (lactide) and poly(glycolide). However, it has been observed that in some circumstances, unfavorable histological responses can occur during the process of degradation through hydrolysis. This is particularly true when there is a large volume of material to be degraded. More particularly, a localized, sterile inflammatory response can initiate a cascade of biological events leading to osteolytic reactions which are radiographically detectable and which compromise local bone quality.

A number of devices have been developed in an attempt to mitigate the aforementioned "stress shielding" issues.

U.S. Pat. No. 4,338,926 (Kummer et al.) discloses a construction in which a layer of biodegradable material is disposed between a bone plate and the bone surface. As this layer of biodegradable material degrades over time, the load carried by the bone increases and the load carried by the bone plate decreases.

U.S. Pat. No. 5,013,315 (Barrows) discloses a construction in which a layer, comprising a mix of biodegradable and non-biodegradable polymer, is disposed between a bone plate and the bone surface.

U.S. Pat. No. 5,935,127 (Border) discloses a metal intramedullary rod having apertures therein for receiving metal transfixing screws. The apertures in the metal rod are initially filled with a biodegradable polymer. During use, the transfixing screws are driven though the polymer; as the polymer resorbs, the screws become loose within the apertures, thereby shifting increasingly more load to the bone.

Japanese Patent Document No. 10085232 A (Hidekazu et al.) discloses the use of a metallic screw with a biodegrable washer. The screw and washer are used to transfix a fracture; as the washer resorbs, the compression is relieved so that the bone carries progressively more of the load.

Unfortunately, however, none of the foregoing constructions has proven entirely satisfactory, for a variety of reasons.

It would, therefore, be a significant improvement in the art to provide an orthopedic fastener which addresses the aforementioned issues of "stress shielding", bone remodeling, implant removal, etc.

SUMMARY OF THE INVENTION

Accordingly, one object of the present invention is to provide a new and improved orthopedic fastener.

Another object of the present invention is to provide a novel orthopedic fastener which is engineered to substantially eliminate bone and/or soft tissue compression after bone and/or soft tissue healing is complete.

And another object of the present invention is to provide a novel orthopedic fastener which minimizes the quantity of biodegradable polymer which must be resorbed by the body.

Still another object of the present invention is to provide a novel orthopedic fastener which is made, in part, from a material which enables bone incorporation or bone replacement.

Yet another object of the present invention is to provide a novel orthopedic fastener which facilitates future orthopedic repairs by inducing bone replacement in the bone area initially occupied by the orthopedic fastener.

And another object of the present invention is to provide a novel method for attaching objects, including bone and/or soft tissue, to bone.

These and other objects are addressed by the present invention which comprises the provision and use of a novel orthopedic fastener. The novel orthopedic fastener comprises a body portion adapted to extend substantially below the surface of a bone, and a head portion adapted to extend substantially above the surface of the bone, wherein the body portion is formed of a first material and the head portion is formed of a second material.

In one preferred form of the invention, the first material comprises a bioabsorbable material which is bioactive so as to encourage tissue in-growth, and the second material comprises a bioabsorbable material which is not bioactive so as to not encourage tissue in-growth.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
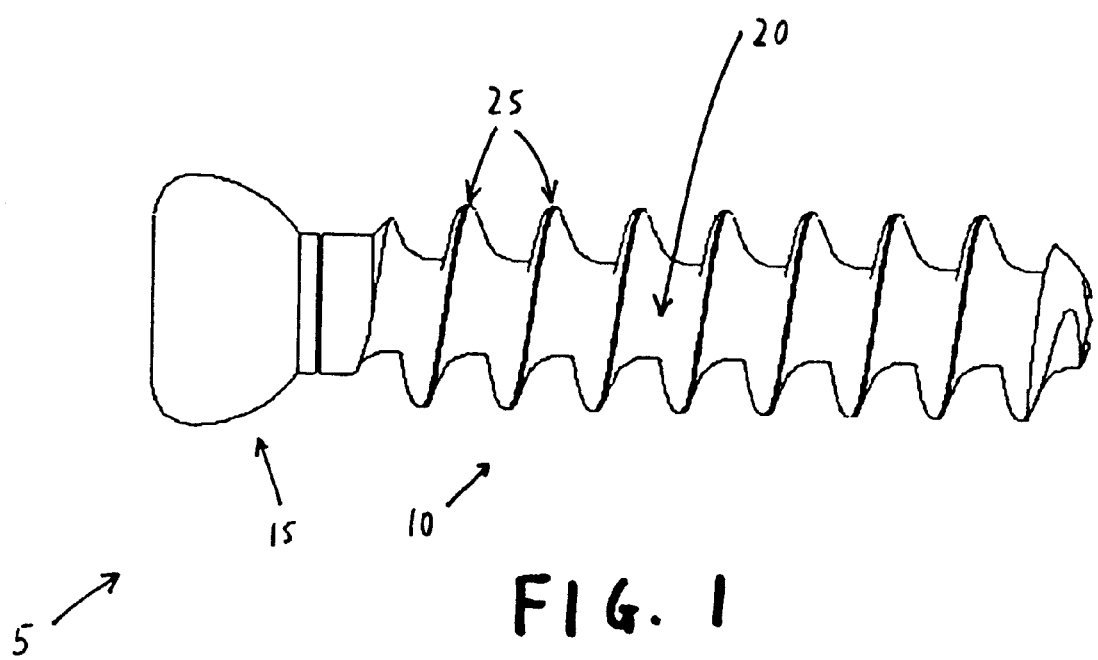
FIG. 1 is a side view of an orthopedic fastener formed in accordance with the present invention.
Figure 2:
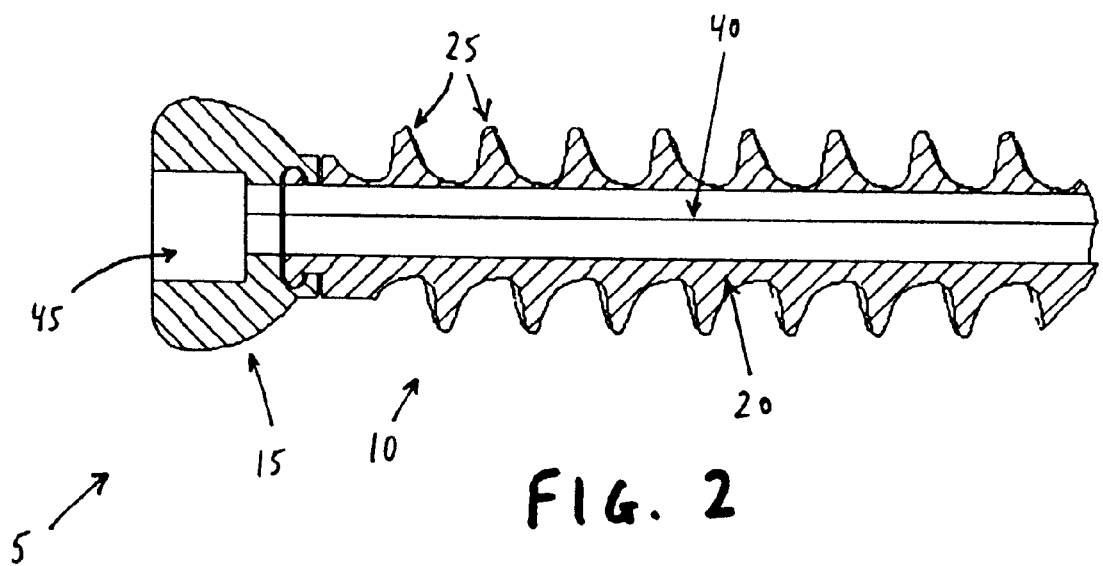
FIG. 2 is sectional view of the orthopedic fastener shown in FIG. 1.
Figure 3:
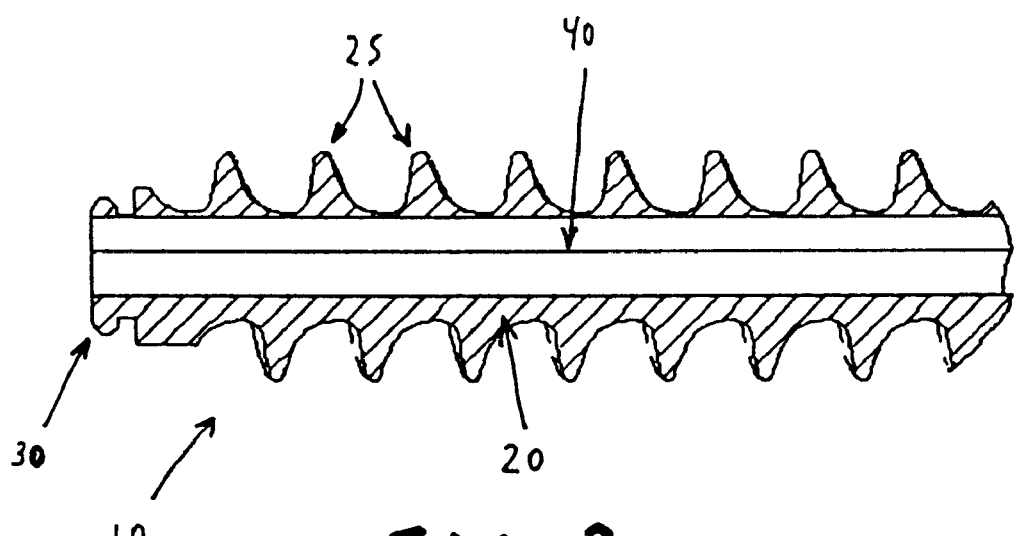
FIG. 3 is a sectional view of the body portion of the orthopedic fastener shown in FIG. 1.
Figure 4:
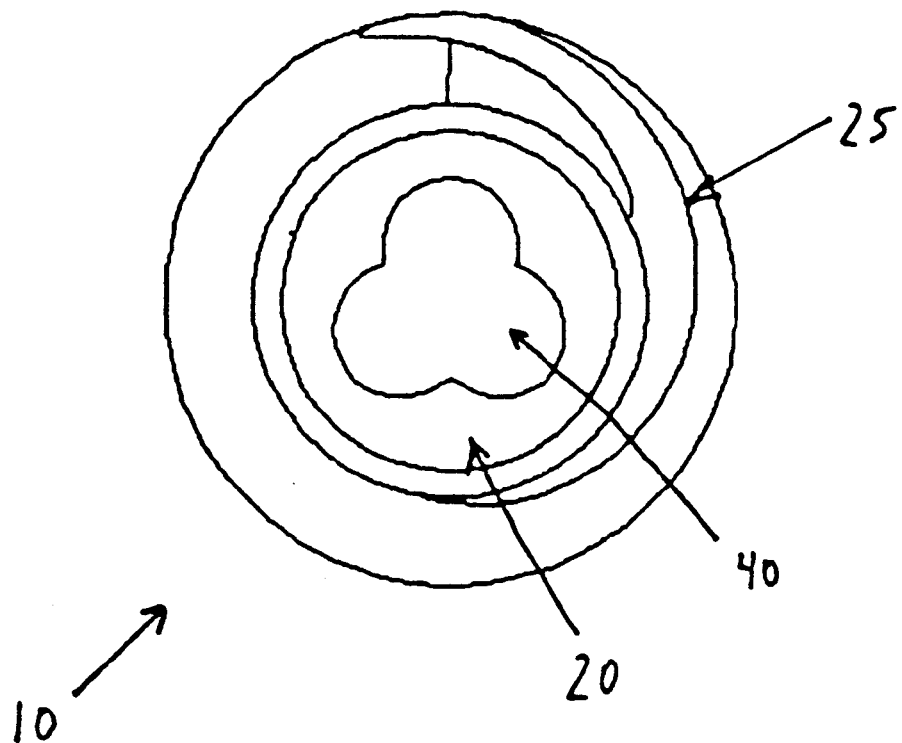
FIG. 4 is a distal end view of the body portion of the orthopedic fastener shown in FIG. 1.
Figure 5:
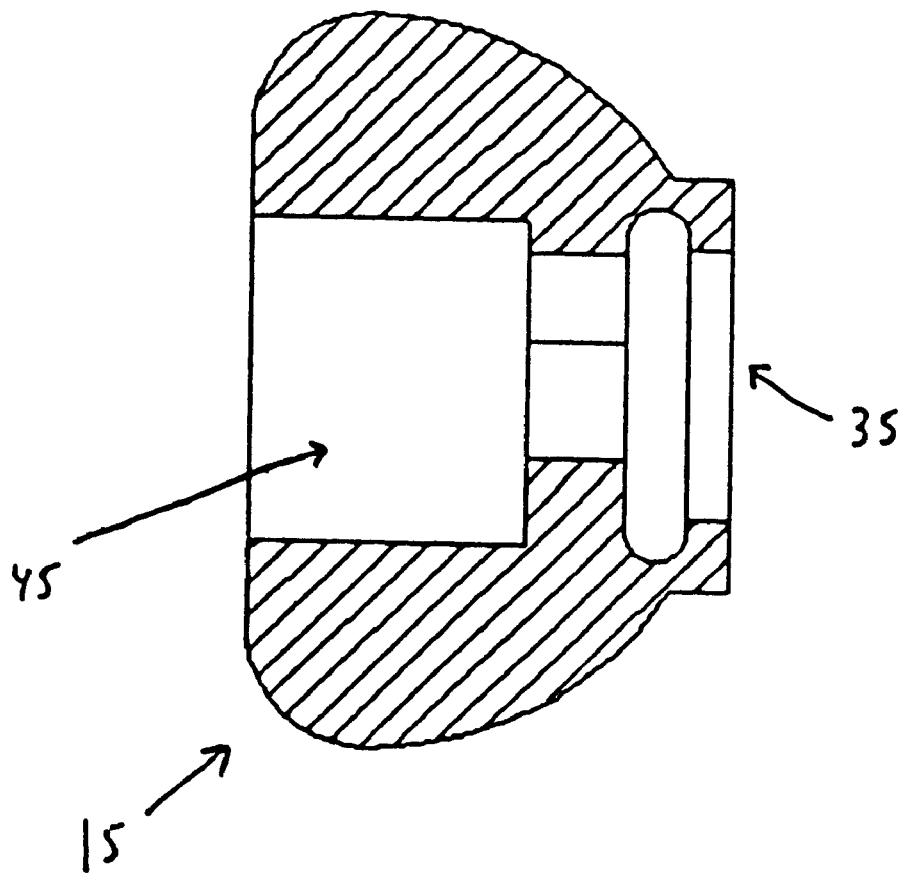
FIG. 5 is an enlarged sectional view of the head portion of the orthopedic fastener shown in FIG. 1.
Figure 6:
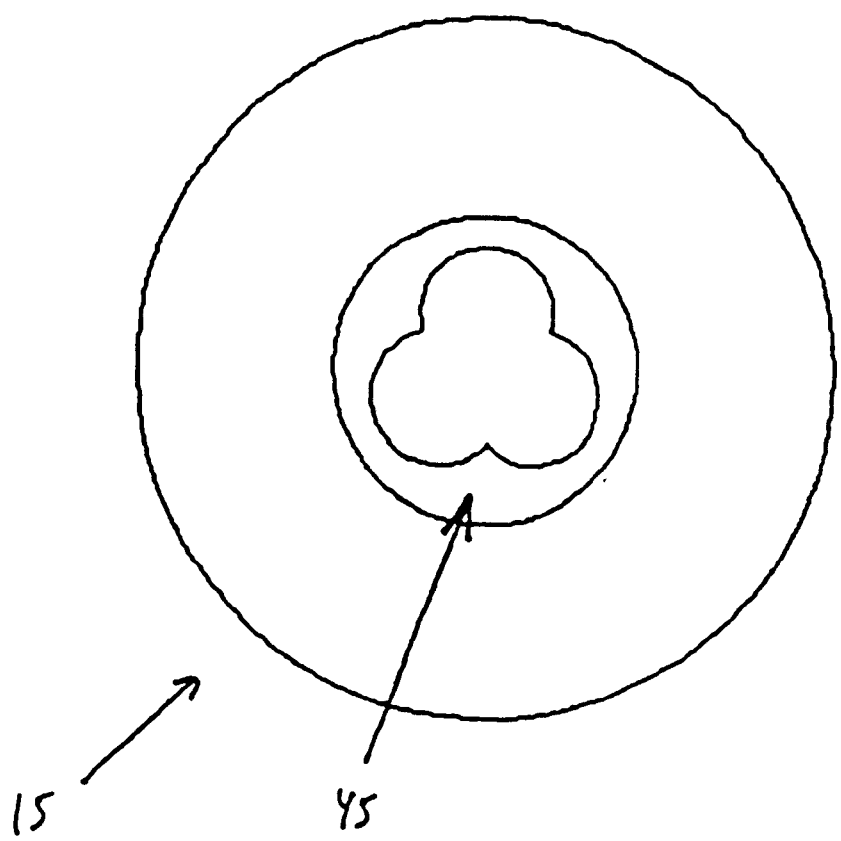
FIG. 6 is a proximal end view of the head portion of the orthopedic fastener shown in FIG. 1.
Figure 7:
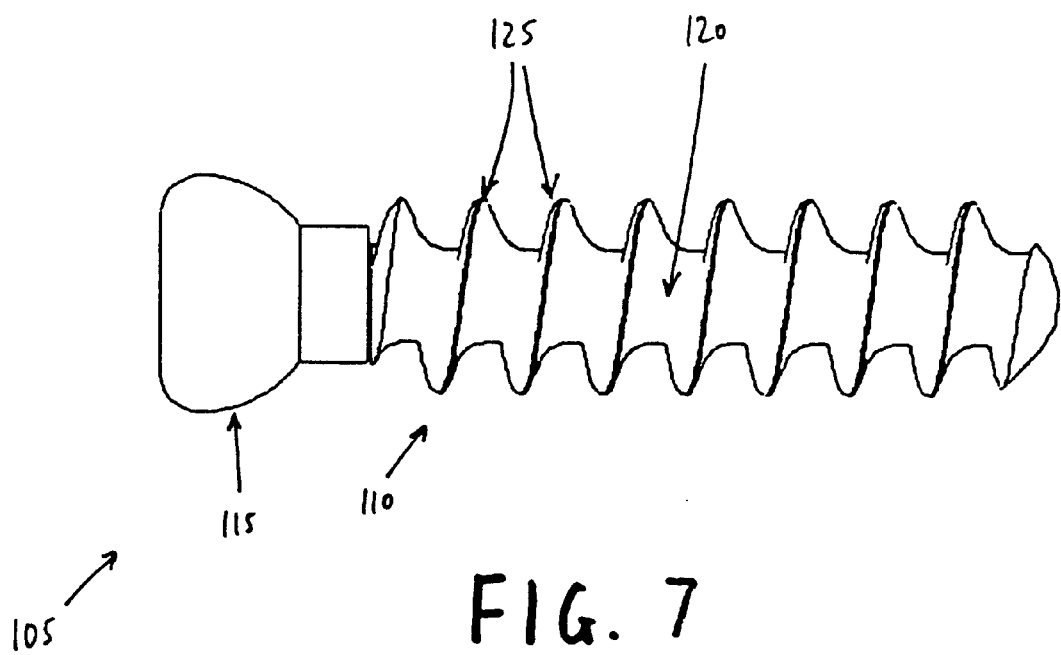
FIG. 7 is a side view of another form of orthopedic fastener formed in accordance with the present invention.
Figure 8:
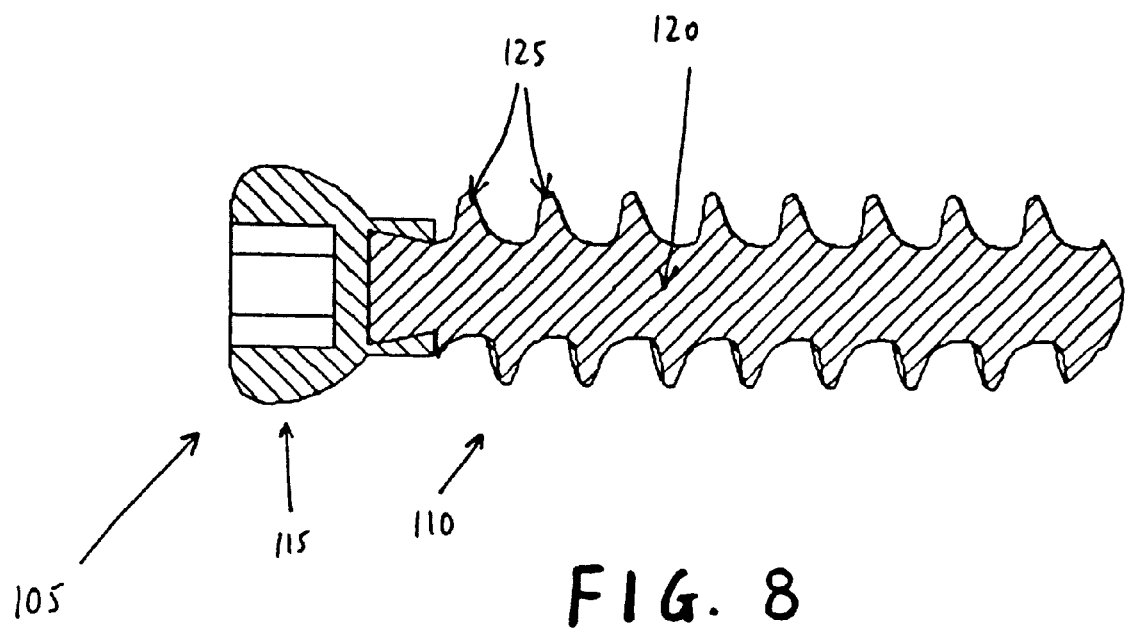
FIG. 8 is a sectional view of the orthopedic fastener shown in FIG. 7.

Looking first at FIGS. 1 and 2, there is shown a novel orthopedic fastener 5 formed in accordance with the present invention. Orthopedic fastener 5 generally comprises a body portion 10 and a head portion 15.

Body portion 10 is shown in detail in FIGS. 1–4. Body portion 10 is adapted to extend substantially below the surface of a bone. Body portion 10 comprises a shank 20 having screw threads 25 formed on the outer surface thereof. Body portion 10 is preferably formed out of a bioabsorbable material which is bioactive so as to encourage tissue in-growth. In one preferred embodiment of the present invention, body portion 10 is formed out of processed bone or an appropriate bioceramic. Where body portion is formed out of bone, bone from a tissue bank is appropriately processed so as to eliminate bacterial, fungal and/or viral transfer, and is shaped, such as by a machining operation, into the desired form. Where body portion 10 is formed out of an appropriate bioceramic, the bioceramic is preferably osteoconductive and osteoinductive. In one preferred embodiment of the present invention, body portion 10 is formed out of a bioceramic such as Bioglass® (USBiomaterials Corp., Alachua, Fla.); Ceravital®, an apatite-glass composite (E. Leitz Wetzlar GmBh, Wetzlar, Germany); Cerabone®, an apatite and beta-Wollastonite glass composite (Japan); Bioverit®, an apatite and phlogopite glass composite (Germany); sintered hydroxyapitite; sintered tricalcium phosphate; and composites thereof.

Head portion 15 is shown in detail in FIGS. 1, 2, 5 and 6. Head portion 15 is adapted to extend substantially above the surface of a bone. In a preferred embodiment, head portion 15 is formed out of a bioabsorbable material which is not bioactive so as to not encourage tissue in-growth. Preferred materials include the aliphatic polyesters of poly(lactide), poly(glycolide), poly(trimethylene carbonate), poly(p-dioxanone) poly($\epsilon$-caprolactone), and copolymers thereof. Other possible polymer materials include the poly (phosphoesters) and the poly(anhydrides).

Body portion 10 and head portion 15 are securely joined to one another so as to form the complete orthopedic fastener 5, with body portion 10 and head portion 15 having complementary mating surfaces 30 (FIG. 3) and 35 (FIG. 5), respectively, so as to transmit axial, bending and torsional forces therebetween. The preferred method of fabrication is to insert injection mold head portion 15 out of a bioabsorbable (but not bioactive) polymer, using the body portion 10 (formed out of a bioabsorbable and bioactive material) as the insert. In this manner, head portion 15 is molded so as to intimately conform to the geometric features of surfaces 30 (FIG. 3) at the proximal end of body portion 10, whereby to form a secure connection. An alternative method of fabrication is a mechanical assembly of body portion 10 and head portion 15.

The present invention provides a novel construction for an orthopedic fastener to optimize the long term results of an orthopedic repair. The extraosseous portion of the fastener (i.e., head portion 15) is a separate component from the intraosseous portion of the fastener (i.e., body portion 10). The extraosseous portion of the fastener is made from a bioabsorbable material which is not bioactive so as to not encourage tissue in-growth. The extraosseous portion retains sufficient mechanical strength at least until the orthopedic repair has healed, and then the extraosseous portion slowly decomposes into by-products which are removed from the repair site by normal metabolic pathways. Once the extraosseous portion is gone, any issues regarding tissue impingement or irritation are eliminated.

The intraosseous portion of the fastener is made from a bioabsorbable material which is bioactive so as to encourage tissue in-growth, i.e., so as to encourage bone on-growth, bone in-growth, and/or bone substitution. This selection of materials eliminates the possibility of an osteolytic reaction such as is commonly found with some of the biodegradable polymers in use today. Furthermore, an intraosseous portion made from a material which leads to replacement by native bone eliminates the possible need for subsequent hardware removal, such as where future repairs or revisions of the original repair are required.

Orthopedic fastener 5 is intended to be set into bone by turning the fastener with a driver. However, since head portion 15 is formed out of a bioabsorbable material which is not bioactive so as to not encourage tissue in-growth, and since most such materials tend to be brittle and carry torsional loads poorly, it is preferred that the driver engage the orthopedic fastener at body portion 10 rather than at head portion 15. Thus, orthopedic fastener 5 includes a non-circular, driver-receiving bore 40 (FIGS. 2–4) in body portion 10, and an over-sized clearance bore 45 (FIGS. 2, 5 and 6) in head portion 15. This construction allows fastener 5 to be rotated by a driver engaging body portion 10 but not engaging head portion 15. Furthermore, it is preferred that the non-circular, driver-receiving bore 40 extend substantially the entire length of body portion 10, whereby the driver can engage body portion 10 over substantially the entire length of body portion 10. This construction is a significant benefit, since allograft and bioceramics also tend to be brittle and can have difficulty accommodating significant torsional loads over relatively small areas. Also, allograft and bioceramics tend to be brittle in bending and, with support established by the driver over the full length of body portion 10, the body portion of fastener 5 is protected from bending loads as well.

Figure 9:
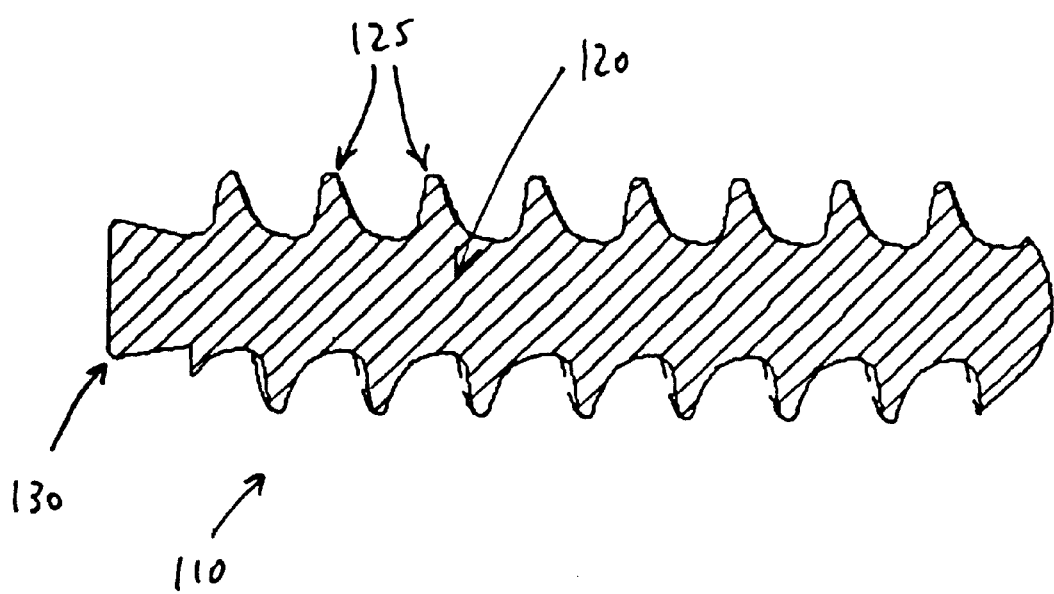
FIG. 9 is a sectional view of the body portion of the orthopedic fastener shown in FIG. 7.
Figure 10:
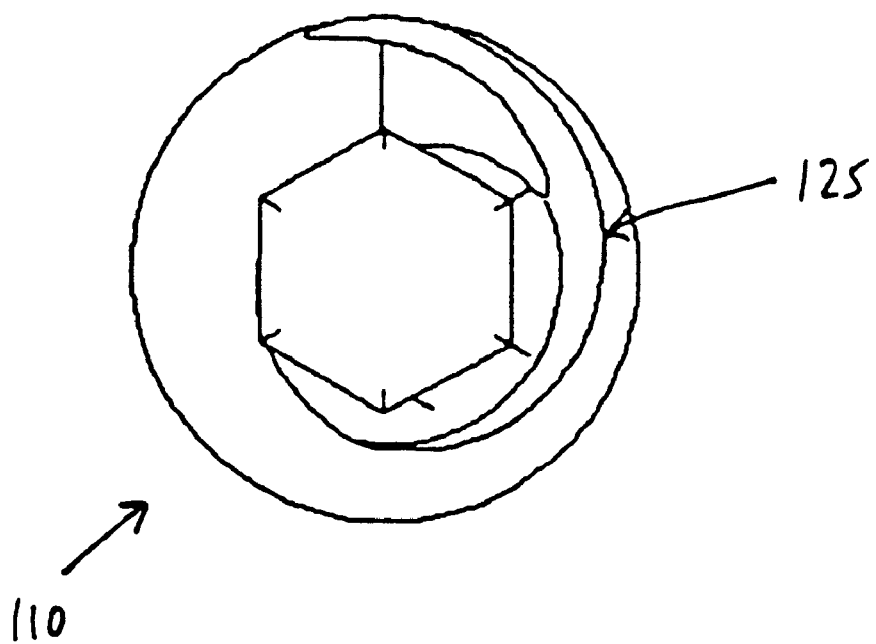
FIG. 10 is a distal end view of the body portion of the orthopedic fastener shown in FIG. 7.
Figure 11:
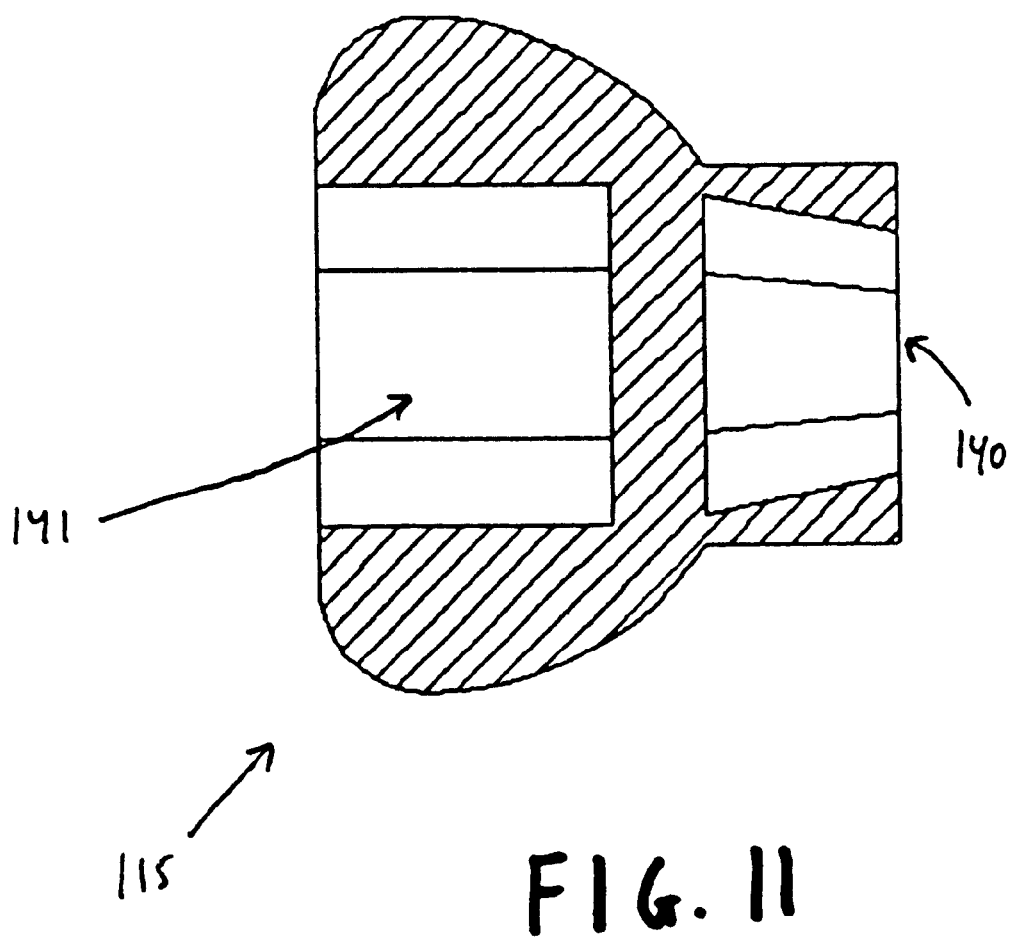
FIG. 11 is an enlarged sectional view of the head portion of the orthopedic fastener shown in FIG. 7.
Figure 12:
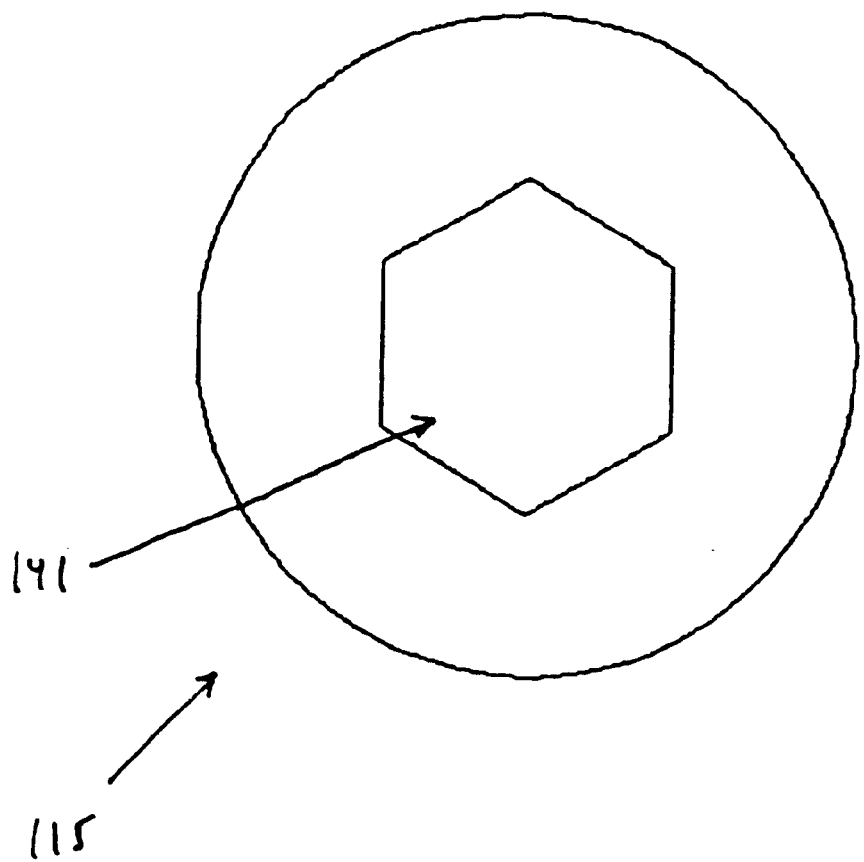
FIG. 12 is a proximal end view of the head portion of the orthopedic fastener shown in FIG. 7.

It is, of course, possible to form the orthopedic fastener of the present invention so that its associated driver engages only the head portion of the fastener. Thus, for example, and looking now at FIGS. 7–12, there is shown an orthopedic fastener 105 which comprises a body portion 110 and a head portion 115, with body portion 110 having a shank 120 and screw threads 125, and with body portion 110 and head portion 115 having complementary mating surfaces 130 (FIG. 9) and 140 (FIG. 11), respectively, so as to transmit axial, bending and torsional forces therebetween. In essence, orthopedic fastener 105 is substantially identical to the orthopedic fastener 5 previously described, except that body portion 110 is not cannulated and head portion 115 has a non-circular, driver-receiving bore 141.

Figure 13:
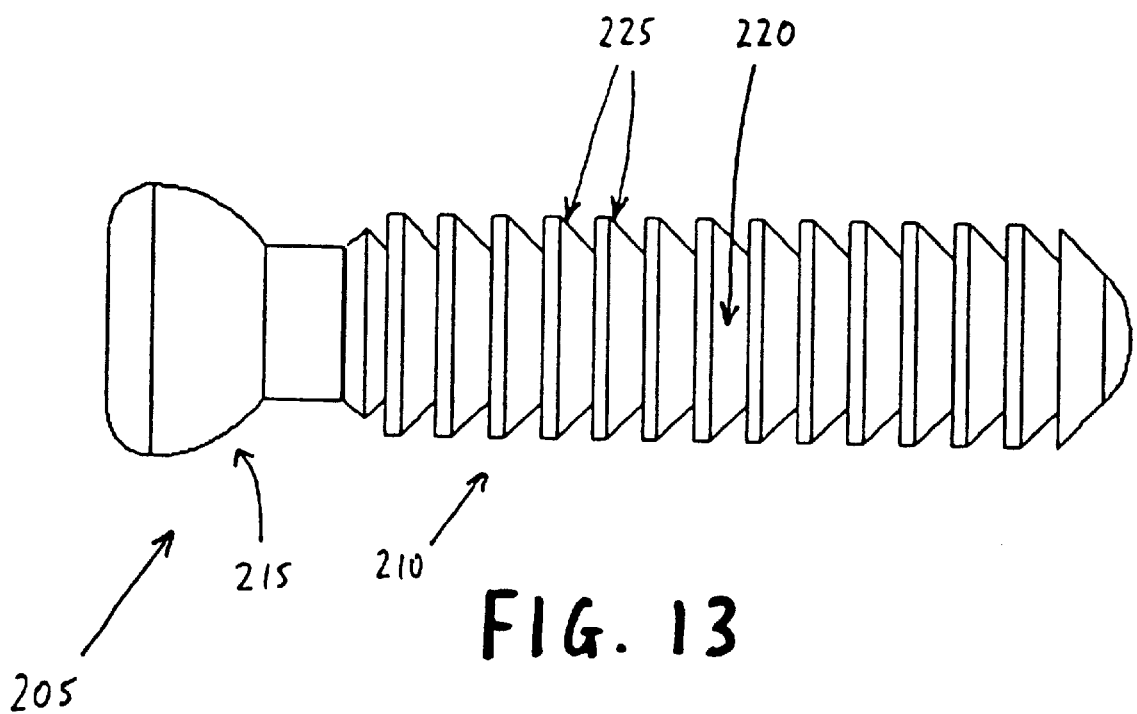
FIG. 13 is a side view of another form of orthopedic fastener formed in accordance with the present invention.
Figure 14:
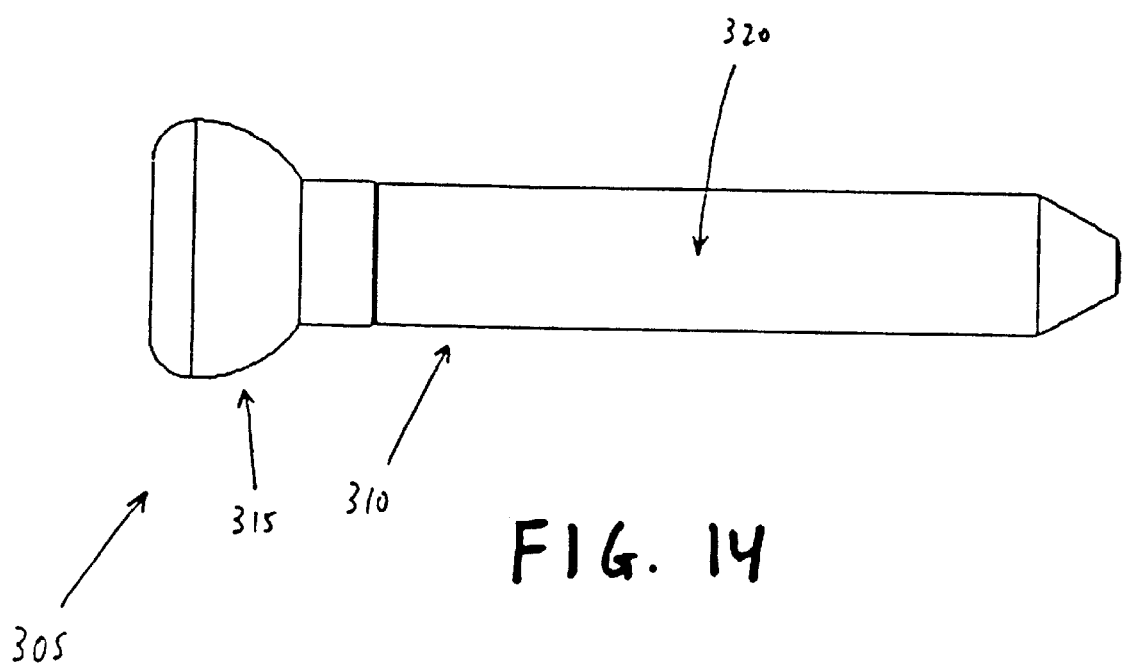
FIG. 14 is a side view of still another form of orthopedic fastener formed in accordance with the present invention.
Figure 15:
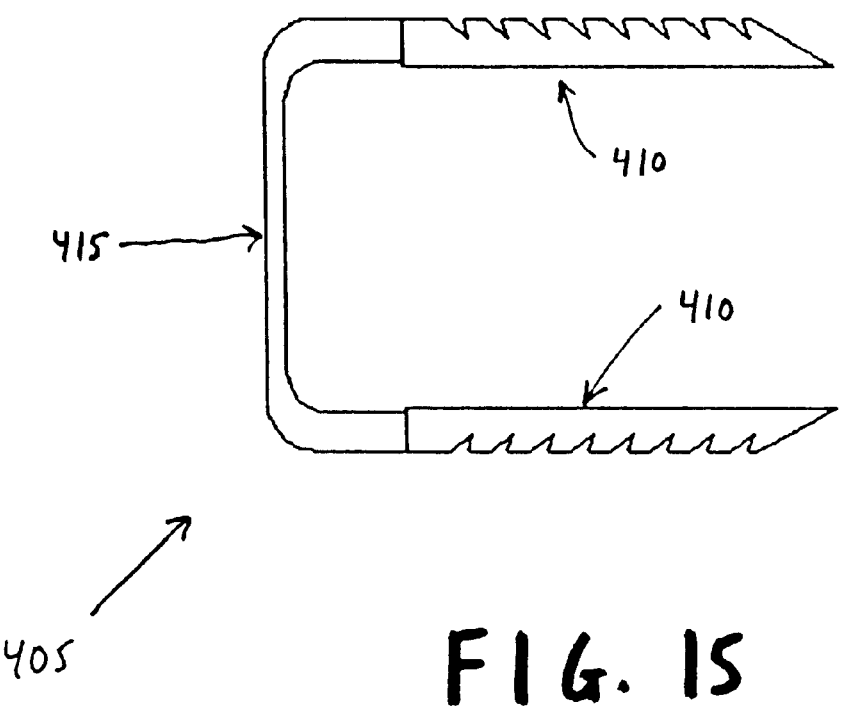
FIG. 15 is a side view of yet another form of orthopedic fastener formed in accordance with the present invention.

It is also possible to form the orthopedic fastener of the present invention without screw threads 25 and 125. Thus, for example, it is possible to form a two-part barbed fastener 205 (FIG. 13) having a body portion 210 and a head portion 215, where barbs 225 are formed on the shank 220 of body portion 210. Or it is possible to form a two-part nail 305 (FIG. 14) having a body portion 310 and a head portion 315, where the shank 320 is substantially smooth. Or it is possible to form a multi-part staple 405 (FIG. 15) having a pair of body portions 410 and a head portion 415.

Figure 16:
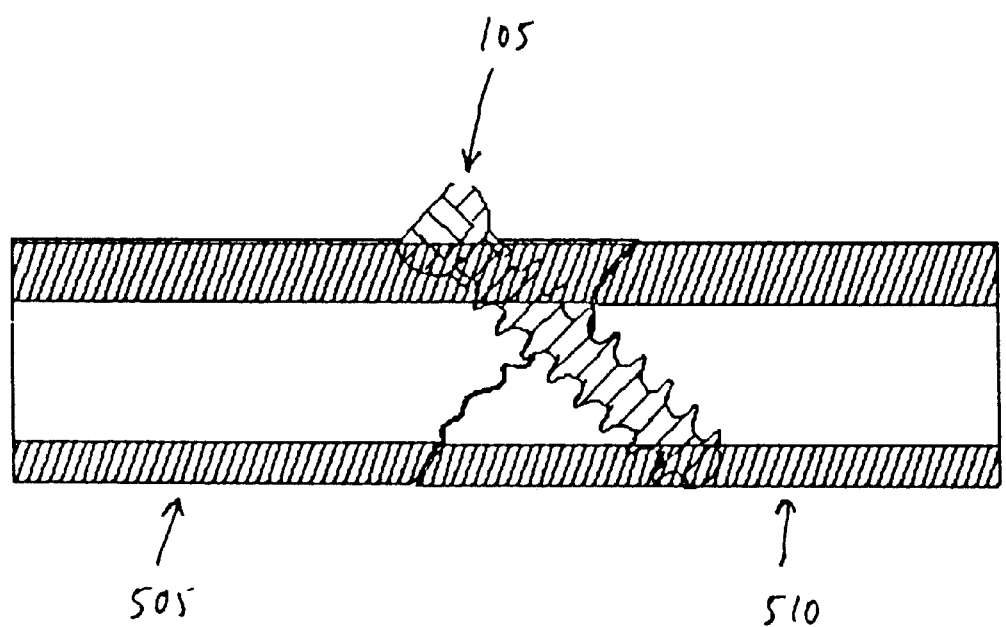
FIG. 16 is a schematic view, partly in section, showing an orthopedic fastener formed in accordance with the present invention transfixing a bone fracture.
Figure 17:
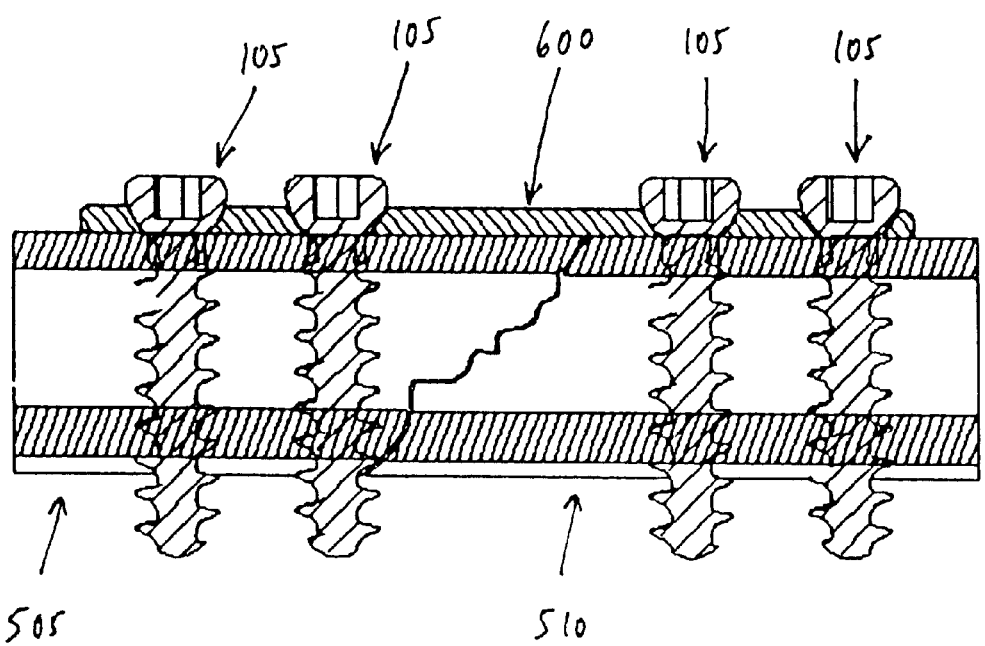
FIG. 17 is a schematic view, partly in section, showing orthopedic fasteners formed in accordance with the present invention securing a bone plate to a fractured bone.
Figure 18:
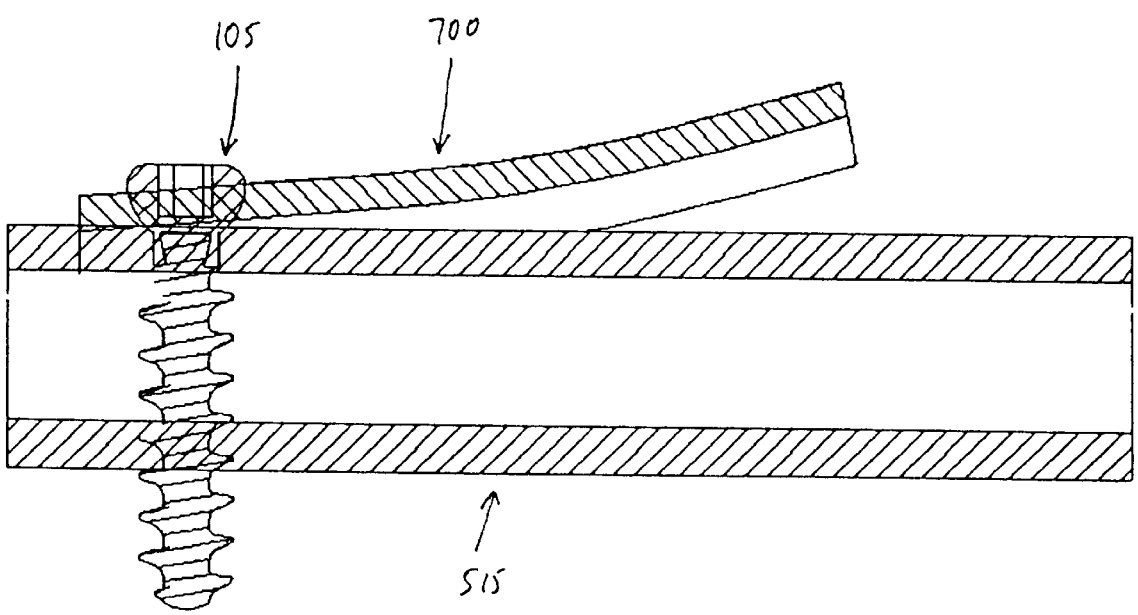
FIG. 18 is a schematic view, partly in section, showing an orthopedic fastener formed in accordance with the present invention attaching soft tissue to bone.

Orthopedic fasteners formed in accordance with the present invention may be utilized in a variety of ways. Thus, for example, FIG. 16 shows a fastener 105 attaching together two portions 505, 510 of bone; FIG. 17 shows a plurality of fasteners 105 securing a bone plate 600 to two portions 505, 510 of a bone, so as to hold those portions together; and FIG. 18 shows a fastener 105 attaching a piece of soft tissue 700 to a bone 515.

In the foregoing description, the body portion of the orthopedic fastener is described as preferably being formed out of a bioabsorbable material which is bioactive so as to encourage tissue in-growth. However, it is also possible to form the body portion out of another type of material. By way of example but not limitation, the body portion may be formed out of a metal, e.g., stainless steel or titanium.

Having thus described preferred embodiments of the invention with reference to the accompanying drawings, it is to be understood that the embodiments shown herein are provided by way of example only, and that various changes and modifications may be effected by one skilled in the art without departing from the scope or spirit of the invention as defined in the claims.

What is claimed is:

1. An orthopedic fastener for the repair of musculoskeletal structures, the fastener comprising:

a body portion adapted to extend substantially below the surface of a bone; and a head portion adapted to extend substantially above the surface of the bone;

wherein said body portion is formed of a first material and said head portion is formed of a second material;

wherein said first material comprises a bioabsorbable material which is bioactive so as to encourage tissue in-growth; and wherein said second material comprises a bioabsorbable material which is not bioactive so as to not encourage tissue in-growth.

2. An orthopedic fastener according to claim 1, wherein said body portion is formed out of bone.

3. An orthopedic fastener according to claim 2 wherein said body portion is formed out of allograft bone.

4. An orthopedic fastener according to claim 1 wherein said body portion is formed out of a bioceramic.

5. An orthopedic fastener according to claim 4 wherein said bioceramic is osteoconductive and osteoinductive.

6. An orthopedic fastener according to claim 5 wherein said bioceramic is chosen from the group consisting of Bioglass® (USBiomaterials Corp., Alachua, Fla.); Ceravital®, an apatite-glass composite (E. Leitz Wetzlar GmBh, Wetzlar, Germany); Cerabone®, an apatite and beta-Wollastonite, glass composite (Japan); Bioverit®, an apatite and phlogopite glass composite (Germany); sintered hydroxyapitite sintered tricalcium phosphate; and composites thereof.

7. An orthopedic fastener according to claim 1 wherein said head portion is formed from a material chosen from the group consisting of aliphatic polyesters of poly(lactide), poly(glycolide), poly(trimethylene carbonate), poly(p-dioxanone) poly($\epsilon$-caprolactone), and copolymers thereof.

8. An orthopedic fastener according to claim 1 wherein said head portion is formed from a material chosen from the group consisting of poly(phosphoesters) and the poly (anhydrides).

* * * * *